(12) United States Patent
Khanna

(10) Patent No.: US 11,504,161 B2
(45) Date of Patent: Nov. 22, 2022

(54) DYNAMIC DECOMPRESSIVE CRANIOTOMY

(71) Applicant: Rohit Khanna, Daytona Beach, FL (US)

(72) Inventor: Rohit Khanna, Daytona Beach, FL (US)

(*) Notice: Subject to any disclaimer, the term of this patent is extended or adjusted under 35 U.S.C. 154(b) by 268 days.

(21) Appl. No.: 16/702,658

(22) Filed: Dec. 4, 2019

(65) Prior Publication Data

US 2020/0197046 A1    Jun. 25, 2020

Related U.S. Application Data

(60) Provisional application No. 62/781,794, filed on Dec. 19, 2018.

(51) Int. Cl.
| | | |
|---|---|---|
| *A61B 17/68* | (2006.01) | |
| *A61B 17/80* | (2006.01) | |
| *A61B 17/84* | (2006.01) | |
| *A61B 17/00* | (2006.01) | |

(52) U.S. Cl.
CPC ........ *A61B 17/688* (2013.01); *A61B 17/8004* (2013.01); *A61B 17/8023* (2013.01); *A61B 17/8061* (2013.01); *A61B 17/846* (2013.01); *A61B 2017/00004* (2013.01)

(58) Field of Classification Search
CPC .............. A61B 17/688; A61B 17/7026; A61B 17/8004; A61B 17/8085
See application file for complete search history.

(56) References Cited

U.S. PATENT DOCUMENTS

| | | |
|---|---|---|
| 5,902,304 A | 5/1999 | Walker et al. |
| 5,916,217 A | 6/1999 | Manthrop et al. |
| 5,993,448 A | 11/1999 | Remmler |
| 6,093,188 A | 7/2000 | Murray |
| 6,187,004 B1 | 2/2001 | Fearon |
| 6,355,036 B1 | 3/2002 | Nakajima |
| 7,229,441 B2 | 6/2007 | Trieu et al. |
| 8,206,425 B2 | 6/2012 | Khanna |
| 9,950,098 B2 | 4/2018 | Khanna |
| 2004/0215192 A1 | 10/2004 | Justis et al. |
| 2005/0107813 A1 | 5/2005 | Gilete Garcia |
| 2007/0185489 A1 | 8/2007 | Abdou |
| 2007/0293865 A1 | 12/2007 | Ko |
| 2008/0154312 A1 | 6/2008 | Colleran et al. |
| 2008/0200954 A1 | 8/2008 | Tucci |
| 2011/0028972 A1 | 2/2011 | Khanna |
| 2011/0028973 A1 | 2/2011 | Khanna |
| 2012/0165879 A1 | 6/2012 | Khanna |

(Continued)

*Primary Examiner* — Olivia C Chang
(74) *Attorney, Agent, or Firm* — Wenderoth, Lind & Ponack, L.L.P.

(57) ABSTRACT

A fixation device includes a first anchor portion configured to join to a first bone portion, a second anchor portion configured to join to a second bone portion, and an intermediate component that extends between the first anchor portion and the second anchor portion. The intermediate component is configured to expand, contract, and angulate enabling constrained movement of the second bone portion with respect to the first bone portion. The second anchor portion has a larger configuration relative to the first anchor portion, thereby preventing the second bone portion from depressing below the first bone portion.

20 Claims, 6 Drawing Sheets

(56) References Cited

U.S. PATENT DOCUMENTS

2012/0184999 A1* 7/2012 Khanna .............. A61B 17/8061
606/281
2012/0277748 A1* 11/2012 Trescony ............... A61B 17/80
606/70
2018/0199963 A1* 7/2018 Ledet ................. A61B 17/7026

* cited by examiner

DYNAMIC DECOMPRESSIVE CRANIOTOMY

FIELD OF DISCLOSURE

One or more embodiments of the present disclosure generally relate to medical devices and methods for utilizing the medical devices. More particularly, one or more embodiments of the present disclosure relate to a device and method for performing a decompressive craniotomy with dynamic bone flap fixation using the device.

BACKGROUND OF THE DISCLOSURE

The following background information may present examples of specific aspects of the prior art (e.g., without limitation, approaches, facts, or common wisdom) that, while expected to be helpful to further educate the reader as to additional aspects of the prior art, is not to be construed as limiting the present disclosure, or any embodiments thereof, to anything stated or implied therein or inferred thereupon. Neurosurgery routinely involves performing craniotomies for exposure of the brain and intracranial contents for various intracranial pathologies including, but not limited to, tumors, head injuries, vascular malformations, aneurysms, infections, hemorrhages, strokes, and brain swelling. A craniotomy typically involves the creation of burr holes and the removal of a portion of the skull (i.e., bone flap) with subsequent healing of the bone flap for closure.

By way of educational background, an aspect of the prior art generally useful to be aware of is that several methods and fixation devices are currently available for re-attaching the bone flap to the skull including small metallic or absorbable plates with screws or wires. Another current method is the use of cranial clamps consisting of two connected circular elements placed on the inside and outside surfaces of the skull. The aforementioned cranial fixation devices generally provide for a rigid fixation of the bone flap to the skull.

In cases of post-operative intracranial hemorrhaging and/or the development of brain swelling, a decompressive craniectomy is typically performed. A decompressive craniectomy is a neurosurgical procedure generally used to treat increased pressure within the skull, herein referred to as intracranial pressure (ICP), from causes such as, but not limited to, head injury, stroke, brain tumor, infection, cerebral hemorrhage, space occupying lesions, hypoxia, hypertension, aneurysm, arteriovenous malformation, venous sinus thrombosis, craniosynostosis, and hydrocephalus. The technique of performing a decompressive craniectomy often involves the removal of a portion of the skull and opening of the dura mater covering the brain, thereby allowing the swollen brain to herniate outwards through the surgical skull defect rather than downwards to compress the brainstem. The procedure generally improves outcomes by lowering ICP. Increased ICP is often debilitating or fatal because this pressure may result in compression of the brain and restriction of cerebral blood flow. A typical aim of a decompressive craniectomy is to reduce this pressure. In general, it is believed that the larger the bone flap, the more ICP is reduced.

Following removal of the bone flap, the dural opening is typically closed with a patch graft taken from a cow, pig, cadaver, or a synthetic graft. A synthetic collagen matrix is often used as a graft since the matrix is capable of expanding. In addition to reducing ICP, studies typically have shown that a decompressive craniectomy may improve cerebral perfusion pressure and cerebral blood flow in patients with head injuries. A decompressive craniectomy may also be used in some cases to treat major strokes associated with malignant brain swelling and increased ICP. It is believed that a decompressive craniectomy typically improves survival and functional outcome in patients with severe brain swelling from causes such as, but not limited to, head injury or stroke, if performed in a timely manner.

There usually is an inherent time delay between diagnosing the cause of the increased ICP and performing a decompressive craniectomy. Typically, once a post-operative increase in ICP is detected, either through a clinical exam or an ICP monitoring device, medical treatment is initiated and CT or MRI imaging is obtained to identify the underlying cause of the increased ICP. If the need for another surgery or a decompressive craniectomy is identified, the anesthesiologist and operating room staff are notified and surgery is generally performed as promptly as possible. Unfortunately, at times, the operating room and/or staff are unavailable, which may increase the time before the surgery can be performed. Despite the best of attempts by the surgeon, in some cases of massive brain swelling or a rapidly developing post-operative hemorrhage, this delay may result in irreversible brainstem injury and, in some cases, a consequent vegetative state or death.

After a craniectomy, it is believed that the risk of brain injury is increased because of the removed bone flap, particularly after the patient heals and becomes mobile again. In addition, there is often an obvious cosmetic skin deformity. Therefore, special measures are generally taken to protect the brain, such as, but not limited to, a helmet or a temporary implant in the skull. Other risks that may arise out of a craniectomy include, without limitation, infection, cerebrospinal fluid leakage, hydrocephalus, encephalomyocele, subdural hygroma and hemorrhage.

Once the patient has healed sufficiently, the craniectomy skull defect is usually closed with a cranioplasty. A cranioplasty typically involves the repair of a defect in the vault of the skull. This repair may be carried out by using bone removed in an earlier surgery that has been preserved or by using bone from elsewhere as a graft. Bone that may be used as a graft may include, without limitation, the iliac bone bounding the pelvis, ribs or a portion of adjacent skull bone. If possible, the original bone flap is generally preserved after the craniectomy in anticipation of the cranioplasty. The bone flap is usually stored sterilely in a freezer until the patient is ready for implantation of the bone flap into the craniectomy skull defect. Typically, this time period can last several months since it may take this long to treat the underlying cause of the increased ICP. This extended time period may result in the increased risk of brain injury and may also cause an increased risk of infection in the stored bone flap. Another technique of storing a removed bone flap typically involves placing the bone flap under the skin in the abdomen of the patient. This technique generally requires a surgical procedure to place the bone flap in the abdomen and another surgical procedure to remove the bone flap, thereby typically increasing consequent risks to the patient.

In cases where the bone flap cannot be replaced due to infection or any other reason, the skull defect is generally repaired with a prosthetic plate or titanium mesh and bone cement. A prosthetic plate typically cannot completely replicate the original skull defect, and therefore some cosmetic deformity often persists following a prosthetic cranioplasty. The prosthesis may also increase the risk of infection. The risks associated with cranioplasty typically include, without limitation, infection, hemorrhage, brain injury, seizures, and death along with other risks inherent to any surgery and general anesthesia. It is also usually necessary for the patient to remain in the hospital for a week or so after a cranioplasty.

By way of educational background, another aspect of the prior art generally useful to be aware of is that some cranial fixation devices describe their use for distraction osteogenesis. Distraction osteogenesis is a surgical process used to reconstruct craniofacial deformities. The bone is fractured into two segments, and the two bone ends of the bone are gradually moved apart during the distraction phase, allowing new bone to form in the gap and reshape the length of the bone. When the desired length is reached, a consolidation phase follows in which the bone is allowed to solidify in the gap. For example, without limitation, one such device describes a telescopic bone plate for use in bone lengthening by distraction osteogenesis. The bone plate is attached to osteomically separated mandible or skull sections by a thread screw assembly. The extent of the required distraction can be adjusted by an external screwdriver.

Another such device describes a skull fixation device typically used for the treatment of craniofacial deformities that provides for relative movement of the skull segments by a percutaneously placed external wrench. Yet another such device describes a mandible or skull expansion plate. The extent of the expansion is adjusted by an externally placed device. Another currently available skull expansion plate comprises a hinged plate at one end and a bone adjuster at the other end comprising two plates with a shaft. The shaft is operated externally to adjust the distance between the bone flap and the skull.

The aforementioned cranial fixation devices in the prior art provide for treatment of craniofacial defects, in particular craniosynostosis. These devices generally require an external screwdriver or other external adjustment means to control the extent of the skull movement allowed and do not typically describe or provide for outward or inward movement of the bone flap relative to the skull in response to a change in the ICP. These devices are also generally placed on the outer surface of the skull and have substantially high profiles which may result in increasing the risk of scalp irritation and palpable cosmetic deformities. One can expect that chronic scalp irritation may cause erosion and exposure of the device through the skin with consequent life threatening infections.

By way of educational background, another aspect of the prior art generally useful to be aware of is that there are multiple methods for performing a decompressive craniectomy. One method of performing a decompressive craniectomy involves attaching the bone flap to the skull with a hinged plate. This method describes attaching the hinged plate to one end of the bone flap and attaching the other end of the bone flap to a rigid plate or no plate at all. The described method typically involves another surgery to fixate the unconstrained bone flap at the rigid plate or plate free end to the skull once the brain swelling subsides. Another method describes a deformable plate which may be used instead of a hinged plate as the bone flap attachment. This construct also typically involves another surgery to fixate the unconstrained bone flap at the straight plate or plate free end of the bone flap. The end of the bone flap attached to the hinged or deformable plate is generally unable to move outwards, and therefore allows limited bone flap movement. Another method involves the use of a two part, sliding device for cranial fixation. This device protrudes outwards from the skull surface and may result in a cosmetic defect, overlying skin irritation, risk of erosion or infection, and typically requires another operation to remove the device once the bone flap heals to the skull. Khanna (U.S. Patent Application Publication No. 2012/0203284) relates a bone flap fixation plate that allows upward and downward bone flap movement and does not prevent the bone flap from sinking inside the skull.

In view of the foregoing, it is clear that these traditional techniques are not perfect and leave room for more optimal approaches.

SUMMARY OF THE DISCLOSURE

The present disclosure relates to a cranial fixation plate for semirigid fixation of a bone flap to the skull following a craniotomy. It provides for constrained outward movement of the bone flap to immediately accommodate for an increase in ICP and subsequently allows the bone flap to move inwards up to the skull once the ICP normalizes. The plate also prevents the bone flap from sinking inside the skull and compressing on the brain. Since the decompressive procedure involves leaving the bone flap in place rather than removing it, as is done in a decompressive craniectomy, this procedure is more appropriately coined as a decompressive craniotomy.

The cranial plate comprises of screw holes for attachment to one end to the bone flap and another end to the skull and an intermediate component that is designed to reversibly expand or contract, as well as angulate, based on the intracranial pressure providing parallel and perpendicular movement between the two end components of the plate. The intermediate component comprises a plurality of bridges extending between the attaching portions with each bridge including an elastic tension spring extendable along the bridge arranged in series. With an increase in ICP, the intermediate expandable component allows the end component attached to the bone flap to move outwards to accommodate the rise in ICP. With subsequent normalization of the ICP, the intermediate tension spring retracts the end component and brings the bone flap back to the skull level. The end of the plate attached to the bone flap is larger than the end of the plate attached to the skull. The larger plate, when positioned overlying the craniotomy kerf, prevents the bone flap from sinking inside the skull and damaging the brain.

An increase in ICP can result from several pathologies including traumatic injury, stroke, hypoxia, hypertension, brain tumor, aneurysm, arteriovenous malformation, infection, venous sinus thrombosis, craniosynostosis, and hydrocephalus. Traumatic injury can be either closed head injury from blunt trauma or penetrating head injury from, for example, a gunshot wound, and usually results in the development of brain swelling and hemorrhage, such as subdural hemorrhage, epidural hemorrhage, subarachnoid hemorrhage, intra-ventricular hemorrhage, brain hemorrhage, and cerebral contusions.

Strokes can be ischemic, hemorrhagic or a combination of both and usually result from cerebral vessel occlusion. Vessel occlusion can be from an arterial embolus from carotid or vertebral artery stenosis, atrial fibrillation, heart septal defect, heart valve abnormalities, heart or aortic aneurysm surgery, carotid or vertebral artery dissection/thrombosis, and vasculitis. Larger strokes result in the development of severe cerebral cytotoxic edema and brain swelling. Treatment of the strokes with antiplatelet therapy or anticoagulation can also lead to the development of cerebral hemorrhage, in some cases, further worsening the brain swelling. Strokes can also be caused by cerebral vessel occlusion from atherosclerotic disease, vasospasm from aneurysmal or traumatic subarachnoid hemorrhage, vasculitis, and a hypercoagulable state.

Cerebral venous sinus occlusion can result in significant diffuse brain swelling as well as hemorrhage. Hypertension is a frequent cause of cerebral hemorrhage particularly deep brain and intraventricular hemorrhage. Severe hypertension can also lead to diffuse brain swelling even without any hemorrhage. Hypoxia from cardiac arrest or apnea can lead to diffuse cerebral cytotoxic injury and consequent brain swelling. Ruptured cerebral aneurysms result in subarachnoid hemorrhage but not infrequently also cerebral and intraventricular hemorrhage with associated hydrocephalus, which can result in significant and immediate rise in ICP. Ruptured arteriovenous malformations can also result in cerebral and intraventricular hemorrhage. Some arteriovenous malformations like Vein of Galen aneurysm can enlarge to a significant size leading to a rise in intracranial pressure without even rupturing.

Brain tumors, either metastatic or primary like gliomas and meningiomas, often cause brain swelling from vasogenic edema. Infections include brain abscess, subdural empyema, epidural abscess, and cerebritis can also lead to significant brain swelling. Seizures can lead to diffuse brain swelling from increased cerebral blood flow and metabolism.

When an increase in ICP exceeds the normal range, the bone flap is pushed outwards enabled by the parallel and perpendicular relative movement of the two plate ends enabled by the intermediate spring component. Once the ICP normalizes, the intermediate spring retracts the two plate ends and approximates the bone flap to the skull. In some instances, two or more of the cranial fixation devices would be used to achieve this form of decompressive craniectomy.

Rather than providing a fixed locked position once implanted, as described in cranial fixation devices in the prior art, the current disclosure allows for constrained outward movement of the bone flap relative to the skull in cases of cerebral swelling and subsequently retracts the bone flap against the skull once the swelling subsides.

In the various embodiments described herein, an exemplary plate configuration is rectangular so as to cover the burr hole or skull opening. Other plate configurations could be circular, semi-circle, square, straight, X-shaped, Y-shaped, fan shaped, or any other configuration able to connect the skull to the bone flap. The plates are very low profile so that they are able to be placed on the outer surface of the skull without any risk for intracranial injury or scalp irritation. The cranial fixation device can be made of titanium or titanium alloy for MRI imaging compatibility. They can also be made of a bio-absorbable material (e.g., polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, the cranial fixation device could made of a radiolucent material (e.g., polyetheretherketone), plastic, or a combination of plastic and metal to reduce CT and MRI imaging artifact.

Although the application for the cranial fixation device described in the various embodiments is for fixation of the bone flap to the skull following a craniotomy and provides for a method of decompressive craniectomy for treatment of increased intracranial pressure, it can also be used to cover a burr hole or skull fracture and treat congenital cranial skull defects like craniosynostosis Various embodiments and advantages of the current disclosure are set forth in the following detailed description and claims which will be readily apparent to one skilled in the art.

BRIEF DESCRIPTION OF THE DRAWINGS

The present disclosure is illustrated by way of example, and not by way of limitation, in the figures of the accompanying drawings and in which like reference numerals refer to similar elements and in which:

FIG. 1 is a diagrammatic top view of the device in a contracted position.

FIG. 2 is a diagrammatic side view of the device, and

FIG. 3 is a diagrammatic top view of the device in an expanded position:

FIG. 4 is a diagrammatic top view of the device in a contracted position.

FIG. 5 is a diagrammatic side view of the device in the contracted position.

FIG. 6 is a diagrammatic top view of the device in an expanded position, and

FIG. 7 is a diagrammatic side view of the device in an expanded position;

FIG. 8 is a diagrammatic top view of the device in a contracted position.

FIG. 9 is a diagrammatic side view of the device in the contracted position, and FIG. 10 is a diagrammatic top view of the device in an expanded position;

FIG. 11 shows a brain in a non-swollen state, and

FIG. 12 shows the brain in a swollen state:

Figure 1:
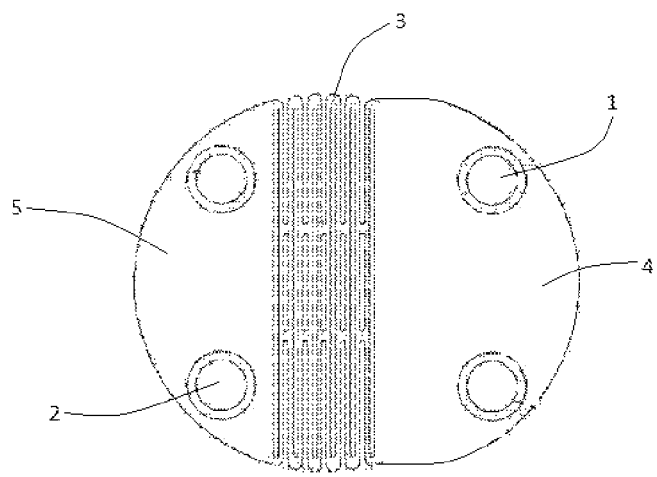
FIGS. 1 through 3 illustrate an exemplary cranial fixation device in accordance with an embodiment of the present disclosure.

Unless otherwise indicated, illustrations in the figures are not necessarily drawn to scale.

DETAILED DESCRIPTION OF THE DISCLOSURE

Embodiments of the present disclosure are best understood by reference to the detailed figures and description set forth herein.

Embodiments of the disclosure are discussed below with reference to the figures. However, those skilled in the art will readily appreciate that the detailed description given herein with respect to these figures is for explanatory purposes as the disclosure extends beyond these embodiments. For example, it should be appreciated that those skilled in the art will, in light of the teachings of the present disclosure, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the disclosure that are too numerous to be listed, but that all fit within the scope of the disclosure. Also, singular words should be read as plural and vice versa and masculine as feminine and vice versa, where appropriate, and alternative embodiments do not necessarily imply that the embodiments are mutually exclusive.

It is to be further understood that the present disclosure is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present disclosure. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this disclosure belongs. Exemplary methods, techniques, devices, and materials are described, although any methods, techniques, devices, or materials similar or equivalent to those described herein may be used in the practice or testing of the present disclosure. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims have been formulated in this application to particular combinations of features, it should be understood that the scope of the present disclosure also includes any novel feature or any novel combination of features disclosed herein either explicitly or implicitly or any generalization thereof, whether or not it relates to the same disclosure as presently claimed in any claim and whether or not it mitigates any or all of the same technical problems as does the present disclosure.

Features which are described in the context of separate embodiments may also be provided in combination in a single embodiment. Conversely, various features which are, for brevity, described in the context of a single embodiment, may also be provided separately or in any suitable subcombination. Further, notice is hereby given that new claims may be formulated to such features and/or combinations of such features during the prosecution of the present application or of any further application derived therefrom.

References to "one embodiment," "an embodiment," "an example embodiment," "various embodiments," etc., may indicate that the embodiment(s) of the disclosure so described may include a particular feature, structure, or characteristic, but not every embodiment necessarily includes the particular feature, structure, or characteristic. Further, repeated use of the phrase "in one embodiment," or "in an exemplary embodiment," does not necessarily refer to the same embodiment, although it may.

As is well known to those skilled in the art, many careful considerations and compromises typically must be made when designing for the optimal manufacture of a commercial implementation of any system, and in particular, the embodiments of the present disclosure. A commercial implementation in accordance with the spirit and teachings of the present disclosure may be configured according to the needs of the particular application, whereby any aspect(s), feature (s), function(s), result(s), component(s), approach(es), or step(s) of the teachings related to any described embodiment of the present disclosure may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Considering the complexities and risks typically involved in the post-operative management of critically ill patients undergoing a craniotomy, a practical embodiment of the present disclosure provides a method and a cranial fixation device for fixing a bone flap to the skull following a craniotomy for immediate treatment of increased ICP that generally avoids the need for performing a subsequent cranioplasty. Many practical embodiments provide cranial fixation following a craniotomy with a fixation device that allows for constrained movement of the bone flap to immediately accommodate an increase in ICP and subsequently enables the bone flap to move inward toward the skull once the ICP normalizes. In many practical embodiments, this fixation device is a flexible and expandable cranial fixation plate. In some practical embodiments, the cranial fixation device comprises spaced anchor portions and an intermediate component extending between the anchor portions which comprises a series of elastic tension spring members allowing for expansion, contraction, and angulation between the two anchor portions.

In order for the device to allow outward bone flap movement, both perpendicular and parallel movement between the two anchor portions is provided. The device is low-profile and also comprises one anchor portion that is larger than another anchor portion. This larger anchor portion, when position covering the craniotomy kerf between the bone flap and the skull, allows the bone flap to move outward, as well as retract down to the level of the skull, but prevents the bone flap from sinking inside the skull, which leads to a depressed skull and can damage the underlying brain. Since the decompressive procedure provided involves leaving the bone flap in place rather than removing the bone flap, as is typically done in a decompressive craniectomy, this procedure is herein referred to as a dynamic decompressive craniotomy.

The present disclosure will now be described in detail with reference to embodiments thereof as illustrated in the accompanying drawings.

Figure 2:
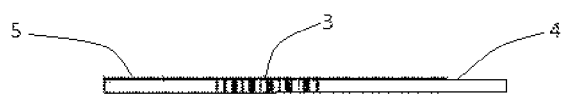
Figure 3:
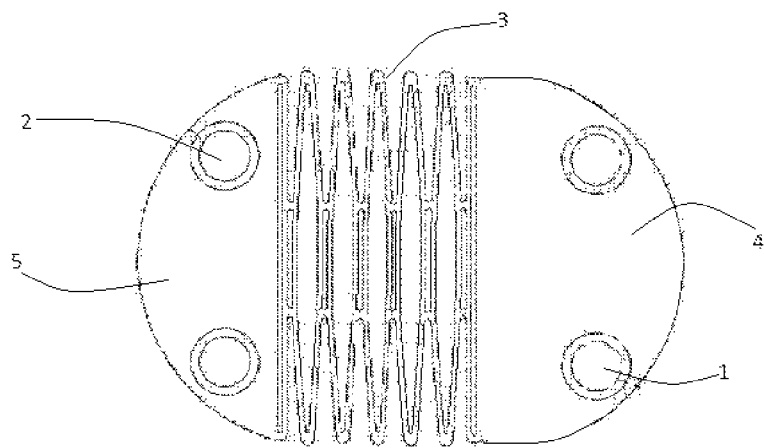

FIGS. 1 through 3 illustrate an exemplary cranial fixation device with a rectangular shape and round ends, in accordance with an embodiment of the present disclosure. FIG. 1 is a diagrammatic top view of the device in a contracted position and FIG. 3 is a diagrammatic top view of the device in an expanded position. FIG. 2 is a side view of the device.

In the present embodiment, the device comprises a larger anchor portion 4 with bone fastener holes 1 for attachment to a bone flap and a smaller anchor portion 5 with bone fastener holes 2 for attachment to a skull. The larger anchor portion 4 has a larger surface area than the smaller anchor portion 5. An intermediate component 3 comprises a series of elastic tension spring members that expand or contract depending on the ICP and allow outward movement of the bone flap relative to the skull.

The tension spring members of intermediate component 3 comprise of a series of parallel, elastically deformable metal strips joined at the strip ends. The contracted position of intermediate component 3 is illustrated by way of example in FIGS. 1 and 2. With an increase in ICP within the skull to which the device is attached, the swollen brain exerts pressure on the bone flap forcing the elastic tension spring members of intermediate component 3 to expand and angulate allowing the larger anchor portion 4 attached to the bone flap to move outward to accommodate the increase in ICP by increasing the skull space.

With subsequent resolution of the brain swelling and normalization of the ICP, the expanded tension spring members of intermediate component 3 contract and return the bone flap to a position substantially even with the skull. In order to allow outward and inward movement of the bone flap relative to the skull, the intermediate component 3 provides not only expansion and contraction, but also angulation. Bone flap outward and inward movement has the larger and smaller anchor portions 4 and 5 move in perpendicular and parallel motion relative to each other enabled by the intermediate portion 3. The larger anchor portion 4 attached to the bone flap when positioned over the craniotomy kerf (i.e., the bone opening defect between the bone flap and skull) and extending to overlap the skull prevents the bone flap from sinking inside the skull and compressing and injuring the brain.

Figure 4:
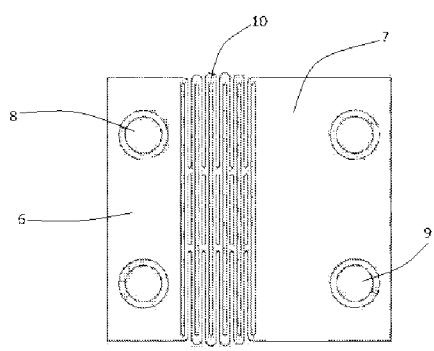
FIGS. 4 through 7 illustrate an exemplary cranial fixation device with a rectangular shape, in accordance with another embodiment of the present disclosure.
Figure 5:
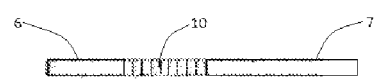
Figure 6:
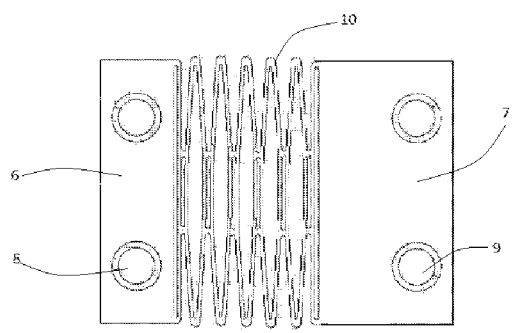
Figure 7:
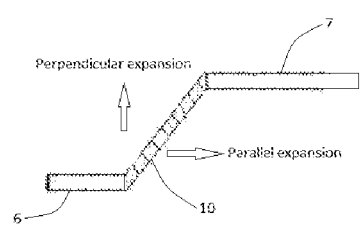

FIGS. 4 through 7 illustrate another exemplary cranial fixation device with a rectangular shape, in accordance with an embodiment of the present disclosure. FIG. 4 is a diagrammatic top view of the device in a contracted position. FIG. 5 is a diagrammatic side view of the device in the contracted position. FIG. 6 is a diagrammatic top view of the device in an expanded position, and FIG. 7 is a diagrammatic side view of the device in an expanded position.

In the present embodiment, a skull attachment smaller anchor portion 6 comprises bone fastener holes 8, and a larger bone flap attachment anchor portion 7 comprises bone fastener holes 9. The smaller and larger anchor portions 6 and 7 are connected by an intermediate component 10 comprising a series of parallel tension springs which are elastically deformable strips joined together at the ends and the middle portions of the strips.

Referring to FIG. 7, this expanded position of the intermediate component 10 allows the bone flap anchor portion 7 to move upward relative to the skull anchor portion 6. This movement includes expansion and angulation of the intermediate portion 10, thereby enabling parallel and perpendicular movement between the smaller and larger anchor portions 6 and 7.

Figure 8:
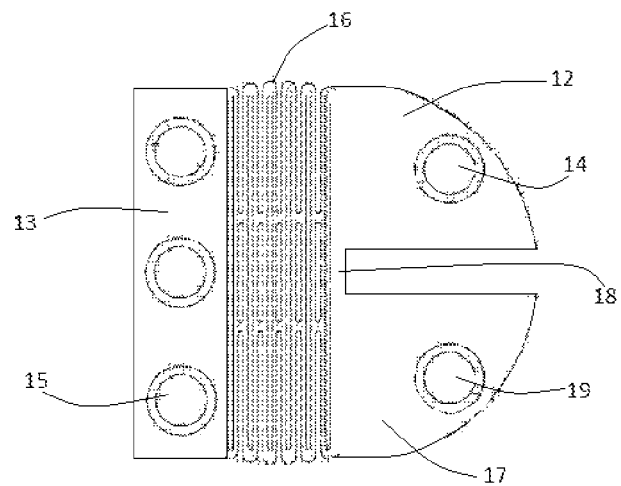
FIGS. 8 through 10 illustrate an exemplary cranial fixation device with a semi-circular shape, in accordance with another embodiment of the present disclosure.
Figure 9:
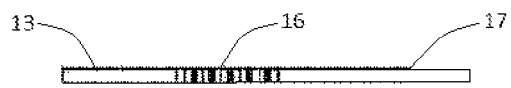
Figure 10:
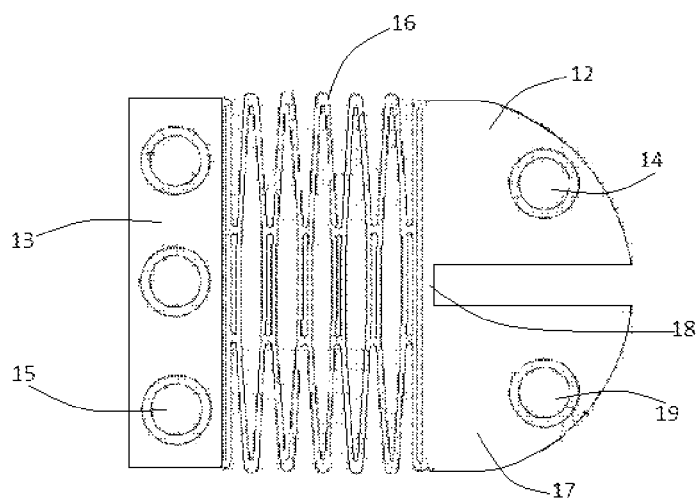

FIGS. 8 through 10 illustrate an exemplary cranial fixation device with rectangular and circular end shapes, in accordance with another embodiment of the present disclosure. FIG. 8 is a diagrammatic top view of the device in a contracted position. FIG. 9 is a diagrammatic side view of the device in the contracted position. FIG. 10 is a diagrammatic top view of the device in an expanded position.

The circular shape of the device may be well suited to cover a burr hole skull defect. In the present embodiment, the device comprises two larger anchor portions 12 and 17 with bone fastener holes 14 and 19, respectively, and a smaller anchor portion 13 with bone fastener holes 15. The larger anchor portions 12 and 17 are connected to the smaller anchor portion 13 by an intermediate component 16. The larger anchor portions 12 and 17 are secured to the bone flap and the smaller anchor portion 13 is secured to the skull with the larger anchor portions 12 and 17 covering the burr hole defect.

The intermediate component 16 comprises a plurality of parallel tension springs that reversibly expand or contract depending upon the pressure exerted on the anchor portion (s) 12 and 17 attached to the bone flap. Typically, intermediate component 16 is designed to expand when the ICP exceeds 20 to 25 mm Hg and to retract when the ICP is normal (i.e., less than 15 to 20 mmHg). It is contemplated that some alternate embodiments may be implemented to expand and retract at different pressures in order to accommodate applications in which the ICP may be higher or lower than normal. The larger anchor portions 12 and 17 are connected to each other by an intermediate component 18. The three anchor portions 12, 17, and 13 can also move independently of each other's positions, thereby allowing for a particularly flexible device.

In the various embodiments described in the foregoing, the configuration of the anchor portions come together to form substantially rectangular, square or circular shapes when in a compressed position. Those skilled in the art will readily recognize, in light of and in accordance with the teachings of the present disclosure, that some alternate embodiments may be implemented with anchor portions with a multiplicity of suitable configurations such as, but not limited to, oval configurations, semi-circle configurations, semi-oval configurations, C-shapes, L-shapes, T-shapes, X-shapes, Y-shapes, Z-shapes, fan shapes, configurations in which the anchor portions differ from each other in size and/or shape, or any other configuration able to connect a skull to a bone flap.

Some alternate embodiments may comprise multiple intermediate components that may or may not be joined to opposite anchor portions. Furthermore, the cranial fixation devices described in the foregoing are illustrated by way of example with unitary construction, such that the anchor portions and intermediate components are formed from a single piece material. Some alternative embodiments contemplate that the components of the cranial fixation devices can be non-integral such that the components may be attached to and/or coupled to other components of the device.

The intermediate components illustrated by way of example in the forgoing comprise substantially parallel tension springs that are connected at the ends or connected at the ends and the middle portions. The expandable intermediate component in some alternate embodiments may comprise a multiplicity of suitable expansion means including, without limitation, tension springs attached at the middle only, tension springs with an accordion-like configuration, expandable mesh material, cross-links, compressed O-shaped, U-shaped, V-shaped, X-shaped or W-shaped members that expand, a plurality of cutouts, a single tension spring, an elastomeric component, a spring, hinged connectors, coiled wire, chain, sliding connectors, an elastic cord, or a combination thereof.

It is contemplated that cranial fixation devices according to many practical embodiments of the present disclosure may be made of a multiplicity of suitable materials including, without limitation, metals such as, but not limited to, titanium or titanium alloy for MRI imaging compatibility. Some embodiments may be made of materials that are typically absorbed by the body over time including, without limitation, allograft, xenograft bone, or a bioresorbable material such as, but not limited to, polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, or para-dioxanone. Alternatively, some embodiments may be made of a radiolucent material such as, but not limited to, polyetheretherketone (PEEK), polyaryletherketone (PEAK), high molecular weight polyethylene, carbon fiber, polyurethane, plastic, or a combination of plastic and metal to reduce CT and MRI imaging artifact. The expandable material of the intermediate components in some embodiments may be made of various different materials such as, but not limited to, silicone, rubber, ethylene propylene compounds, flourocarbon, polyurethane, titanium, other metal components designed to reversibly expand and/or contract, etc.

In many practical embodiments, the thickness of the device generally ranges from 0.3 mm to 20 mm. The size of the anchor portions generally range from 6 mm to 40 mm. The expandable intermediate component of the cranial fixation device is typically capable of reversibly expanding from 1 to 1000% of its contracted size. While the above-mentioned size ranges of the device components reflect many practical embodiments, some alternate embodiments may comprise components outside of the aforementioned ranges.

In some alternate embodiments, the cranial fixation device comprises anchor portions that are relatively small in size in relation to an expandable intermediate component that connects the anchor portions. The intermediate component comprises a series of compressed, oval-shaped tension springs which are capable of reversibly expanding into wider diamond shapes. It is contemplated that cranial fixation devices similar to the devices illustrated may comprise more or fewer holes for bone fasteners or bone screws, tension springs of various different shapes, and/or other types of expanding means, etc. Furthermore, some alternate embodiments may be implemented in various different configurations such as, but not limited to, rectangular configurations with four anchor portions and four intermediate components, triangular configurations, L-shaped configurations, T-shaped configurations, V-shaped configurations, X-shaped configurations, Z-shaped configurations, etc.

Figure 11:
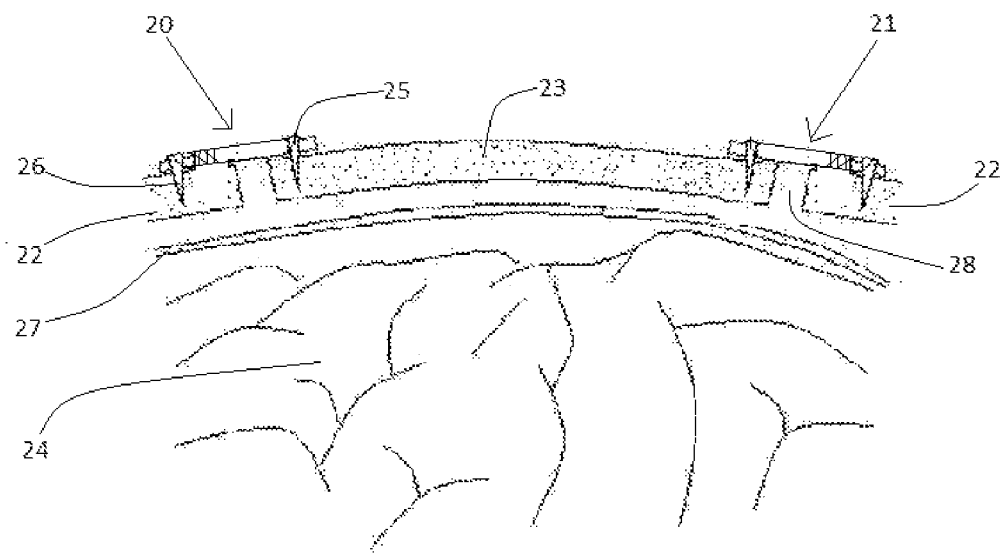
FIGS. 11 and 12 are cross sectional side views of exemplary cranial fixation devices attached to a skull and a bone flap for a dynamic decompressive craniotomy, in accordance with another embodiment of the present disclosure.
Figure 12:
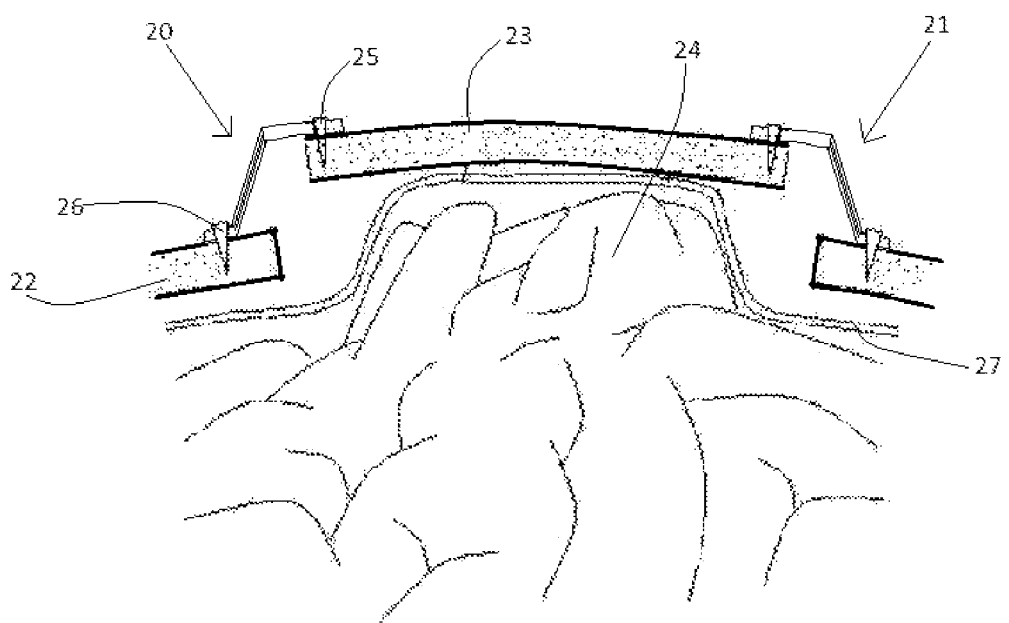

FIGS. 11 and 12 are cross sectional side views of exemplary cranial fixation devices 20 and 21, each of which can be any of the above-described embodiments of the exemplary cranial fixation device, attached to a skull 22 and a bone flap 23 for a dynamic decompressive craniotomy, in accordance with another embodiment of the present disclosure. FIG. 11 shows a brain 24 in a non-swollen state, and FIG. 12 shows the brain 24 in a swollen state.

In the present embodiment, the cranial fixation device 20 is attached to the bone flap 23 with a screw 25 and is attached to skull 22 with a screw 26. The cranial fixation device 21 is similarly attached. The length of the screws 25 and 26 can range from 4 mm to 20 mm. In some alternate embodiments, the cranial fixation devices may be attached to the skull and bone flap with larger or smaller screws, with spikes, with a combination of screws on one anchor portion and spikes on the other anchor portion, etc. In other alternate embodiments, the cranial fixation device may comprise various different attachment means such as, but not limited to, clamps which are attached to the skull and/or bone flap, self-tapping screws, self-drilling screws, pins, rivets, wires, sutures, clamps, claws, spikes, hooks, adhesives, etc. In some instances, as illustrated in FIGS. 11 and 12, two or more cranial fixation devices 20 and 21 are used to affix the bone flap 23 to the skull 22.

Referring to FIG. 11, the brain 24 and a dura 27 are in a normal position. Referring to FIG. 12, with the development of swelling of the brain 24 or an increase in ICP from a hemorrhage or other causes, the brain 24 pushes against the bone flap 23. The pressure on the bone flap 23 expands the intermediate components of cranial fixation devices 20 and 21, thereby allowing the anchor portions attached to the bone flap 23 to move outward relative to the anchor portions attached to the skull 22 to accommodate the swelling of the brain 24.

Referring to FIG. 11, once the swelling subsides, the cranial fixation devices 20 and 21 draw back to their contracted positions, and the bone flap 23 moves back towards skull 22. The larger anchor portions of the cranial fixation devices 20 and 21 attached to the bone flap 23 overlap the craniotomy kerf 28 and prevent the bone flap 23 from sinking inside the skull 22 and compressing on the brain 24.

Normal ICP is typically less than 20 mm Hg, and with any brain swelling or hemorrhage, ICP can increase to greater than 20 mm Hg. With an increase in ICP above the normal range, the semirigid cranial fixation devices are designed such that the intermediate components lengthen and angulate into an extended position from a contracted position enabling the two anchor portions of each device to move apart in a parallel and perpendicular motion, thereby allowing the bone flap to move outwards from the skull in a constrained manner to accommodate the higher ICP. Once the ICP returns to below 20 mm Hg, the intermediate components retract and position the bone flap downwards to substantially the same level as the skull and the larger anchor portions prevent the bone flap from sinking inside the skull.

Figure 13:
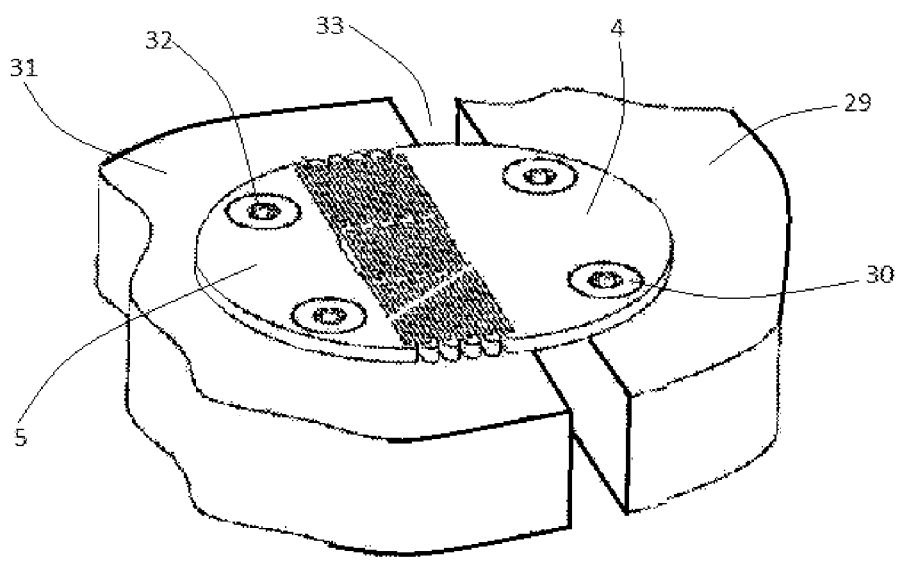
FIG. 13 is a side perspective view of an exemplary cranial fixation device in place to secure a bone flap to a skull by a decompressive craniectomy, in accordance with another embodiment of the present disclosure.

FIG. 13 illustrates the embodiment of FIG. 1 with the larger anchor portion 4 attached to a bone flap 29 with screws 30 and the smaller anchor portion 5 attached to a skull 31 with screws 32. The larger anchor portion 4 is positioned to overlap a craniotomy kerf 33 between the bone flap 29 and skull 31 thereby preventing the bone flap 29 to be depressed below the skull level.

Figure 14:
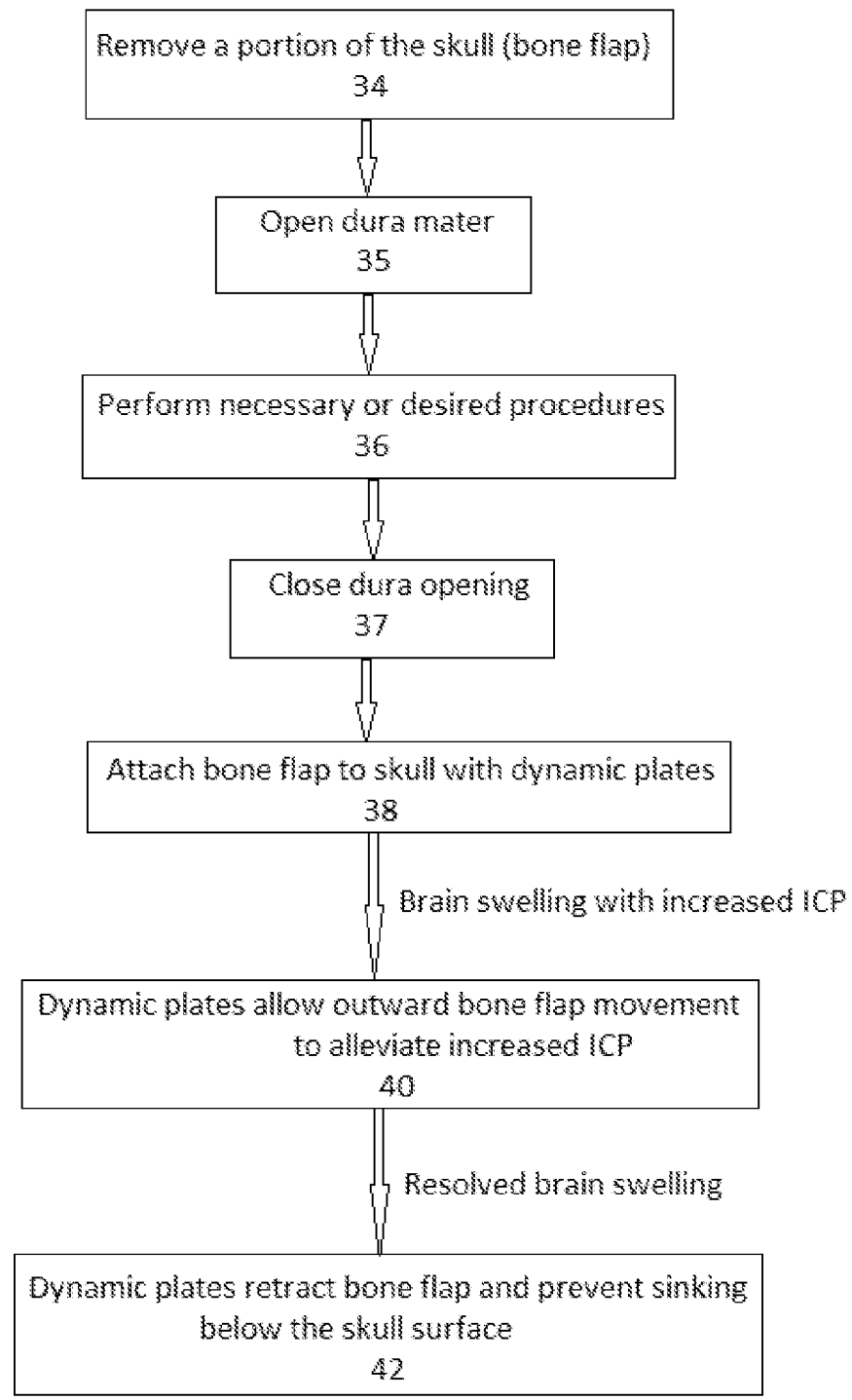
FIG. 14 is a flowchart illustrating an exemplary method for a dynamic decompressive craniotomy, in accordance with another embodiment of the present disclosure.

FIG. 14 is a flowchart illustrating an exemplary method for a dynamic decompressive craniotomy, in accordance with an embodiment of the present disclosure. A decompressive craniotomy is typically performed to reduce increases in the ICP of a patient, which may be caused by a variety of factors or occurrences. In the present embodiment, the process begins in step 34 by removing a portion of the skull known as a bone flap.

In step 35, the dura mater covering the brain is opened, thereby allowing the swollen brain to herniate outwards through the surgical skull defect. In general, it is believed that the larger the bone flap removed in step 34 is, the more the ICP is reduced. With the removal of the bone flap and the opening of the dura mater, the practitioners may take this opportunity to perform necessary or requested procedures on the brain of the patient in step 36 such as, but not limited to, hematoma evacuation, biopsies, tumor removal, repairing an injury, placing a shunt, etc.

The dural opening is typically closed in step 37. The dura closure material is often a collagen matrix that allows for expansion. Alternatively, other dural substitutes may be used such as, but not limited to, grafts made from autograft, allograft, or xenograft material or grafts taken from cows, pigs, cadavers, etc. In an alternate embodiment, this step may be skipped, and the dura may be left partially open with slits.

In the present embodiment, the bone flap is replaced and attached to the skull by one or more dynamic expandable devices (i.e., one or more embodiments of the present disclosure) in step 38. In some instances, two more of the dynamic devices are used to achieve this form of decompressive craniotomy. Alternatively, an expandable cranial fixation device can be placed on one side of the bone flap and a hinge device can be placed on the other side. In the present embodiment, the anchor portions of the cranial fixation devices are positioned on the surfaces of the skull and the bone flap to hold the bone flap substantially level with the skull when the expandable intermediate component of the fixation devices are contracted and to allow external movement of the bone flap relative to the skull in case of an increase in the ICP.

When an increase in the ICP exceeds the normal range, the bone flap is pushed outwards and causes the expandable intermediate components of the cranial fixation devices to stretch and angulate into an extended position in step 40. The external movement of the bone flap increases the intracranial space to accommodate the increase in the ICP and provides for a decompressive craniotomy. Following normalization of the ICP, the bone flap is compressed back towards the skull by the cranial fixation device, which also prevents the bone flap from sinking inside the skull and compressing on the brain in step 42.

Although the application for the cranial fixation device described in the present embodiment is for fixation of the bone flap to the skull following a craniotomy and to provide for a decompressive craniotomy to treat increased ICP, cranial fixation devices according to various embodiments of the preset disclosure may be used to treat ICP resulting from various different causes such as, but not limited to, traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, or seizure, etc. Moreover, some embodiments may be used in different types of applications including, but not limited to, covering a burr hole, repairing a skull fracture, treating congenital cranial skull defects such as, but not limited to, craniosynostosis, etc.

Those skilled in the art will readily recognize, in light of and in accordance with the teachings of the present disclosure, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine including, for example, a processor and a memory, a typical computer system can, when appropriately configured or designed, serve as a computer system in which those aspects of the disclosure may be embodied.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present disclosure, other equivalent or alternative methods of providing an expandable fixation device according to the present disclosure will be apparent to those skilled in the art. The disclosure has been described above by way of illustration, and the specific embodiments disclosed are not intended to limit the disclosure to the particular forms disclosed. For example, the particular implementation of the anchor portions may vary depending upon the particular type of item on which the anchor portions are to be attached. The anchor portions described in the foregoing are directed to cranial implementations that attach to the skull. However, similar techniques are to provide expandable fixation devices with various different types of anchor portions for use in different areas of the anatomy such as, but not limited to, ribs, vertebrae, other bones, soft tissue, etc. Non-cranial implementations of the present disclosure are contemplated as within the scope of the present disclosure. The disclosure is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A fixation device comprising:
   first anchor portion configured to join to a first hone portion;
   a second anchor portion configured to join to a second bone portion; and
   an intermediate component extending between the first anchor portion and the second anchor portion, the intermediate component being configured to expand and angulate enabling parallel and perpendicular movement between the first and the second anchor portions,
   wherein the first anchor portion, the second anchor portion and the intermediate component are coplanar, and
   wherein the first anchor portion has a larger surface area relative to the second anchor portion to prevent the first bone portion from perpendicular movement below a level of the second anchor portion.

2. The fixation device as recited in claim 1, wherein the first anchor portion is adapted to extend from the first bone portion to the second bone portion.

3. The fixation device as recited in claim 1, wherein the intermediate component comprises at least one spring member.

4. The fixation device as recited in claim 1, wherein the intermediate component comprises a series of elastic tension spring members.

5. The fixation device as recited in claim 1, wherein the first anchor portion, the second anchor portion and the intermediate component are formed from a single piece of material.

6. The fixation device as recited in claim 1, further comprising additional anchor portions joined to the intermediate component.

7. The fixation device as recited in claim 6, wherein the intermediate component comprises a plurality of spring members joined to the additional anchor portions.

8. The fixation device as recited in claim 1, wherein the fixation device comprises a material generally absorbable by a body.

9. The fixation device as recited in claim 1, wherein the fixation device comprises a material generally absorbable by a body.

10. The fixation device as recited in claim 1, wherein along a line bisecting the fixation device in the plan view, a length of the first anchor portion is greater than a length of the second anchor portion.

11. The fixation device as recited in claim 1, wherein the first anchor portion and the second anchor portion are free from overlap in the plan view.

12. The fixation device as recited in claim 1, wherein
the first anchor portion comprises a first section, a second section, and a cutout portion between the first section and the second section that extends along a line bisecting the fixation device in the plan view, and
the first section and the second section are connected at an end of the first anchor portion closest to the intermediate component.

13. A fixation device comprising:
a first anchor portion configured to join to a skull bone, the first anchor portion comprising at least one aperture;
a first bone fastener component configured to join the first anchor portion to the skull bone at the aperture of the first anchor portion;
a second anchor portion configured to join to a bone flap of the skull bone following a craniotomy, the second anchor portion being larger in size than the first anchor portion and comprising at least one aperture;
a second bone fastener component configured to join the second anchor portion to the bone flap at the aperture of the second anchor portion; and
an intermediate component extending between the first anchor portion and the second anchor portion, the intermediate component comprising at least one spring member configured to expand to enable constrained movement of the second anchor portion and the bone flap with respect to the first anchor portion and the skull in response to an increase in intracranial pressure and to contract with normalizing intracranial pressure,
wherein the first anchor portion, the second anchor portion and the intermediate component are coplanar.

14. The fixation device as recited in claim 13, wherein the intermediate component is configured to expand with parallel and perpendicular movement between the first and second anchor portions.

15. The fixation device as recited in claim 13, wherein the at least one spring member is a plurality of spring members.

16. The fixation device as recited in claim 9, wherein the intermediate component comprises a series of elastic tension spring members.

17. The fixation device as recited in claim 13, wherein the first anchor portion, the second anchor portion and the intermediate component are formed from a single piece of material.

18. The fixation device as recited in claim 13, further comprising additional anchor portions joined to the intermediate component.

19. The fixation device as recited in claim 18, wherein the intermediate component comprises a plurality of spring members joined to the additional anchor portions.

20. The fixation device as recited in claim 13, wherein the first anchor portion is configured to extend from the first hone portion to the second bone portion.

* * * * *